(12) United States Patent
Cramer

(10) Patent No.: US 9,518,983 B2
(45) Date of Patent: Dec. 13, 2016

(54) LAYERING FOR SEPARATING PARTICLES

(75) Inventor: Janina Cramer, Haan (DE)

(73) Assignee: QIAGEN, GmbH, Hilden (DE)

( * ) Notice: Subject to any disclaimer, the term of this patent is extended or adjusted under 35 U.S.C. 154(b) by 864 days.

(21) Appl. No.: 13/257,188

(22) PCT Filed: Mar. 25, 2010

(86) PCT No.: PCT/EP2010/053865
§ 371 (c)(1),
(2), (4) Date: Dec. 6, 2011

(87) PCT Pub. No.: WO2010/108971
PCT Pub. Date: Sep. 30, 2010

(65) Prior Publication Data
US 2012/0077285 A1    Mar. 29, 2012

(30) Foreign Application Priority Data

Mar. 25, 2009    (DE) .................. 10 2009 001 864

(51) Int. Cl.
*G01N 33/543*        (2006.01)
*B03C 1/00*           (2006.01)
*C12N 15/10*          (2006.01)

(52) U.S. Cl.
CPC .......... *G01N 33/54326* (2013.01); *B03C 1/00* (2013.01); *C12N 15/1013* (2013.01); *B03C 2201/18* (2013.01)

(58) Field of Classification Search
CPC ................. G01N 35/0098; G01N 33/54326; G01N 27/745; G01N 2030/009; G01N 1/34; G01N 2035/00524
USPC ........................................... 436/526
See application file for complete search history.

(56) References Cited

U.S. PATENT DOCUMENTS

| | | | | |
|---|---|---|---|---|
| 5,770,388 A | * | 6/1998 | Vorpahl | 435/7.25 |
| 6,020,211 A | * | 2/2000 | Tuunanen | 436/526 |
| 6,027,945 A | * | 2/2000 | Smith et al. | 436/526 |
| 6,040,192 A | * | 3/2000 | Tuunanen | 436/177 |
| 2003/0073110 A1 | * | 4/2003 | Aritomi et al. | 435/6 |

FOREIGN PATENT DOCUMENTS

WO    WO 2006/071770 A2    7/2006

OTHER PUBLICATIONS

Anonymous, "MagMAX™ Express 96 User Manual", Jun. 2008, XP002585996 Retrieved from the Internet: URL:http://www.ambion.com/techlib/prot/fm_4387988.pdf> [retrieved on Jun. 7, 2010].

\* cited by examiner

*Primary Examiner* — Mark Shibuya
*Assistant Examiner* — Pensee Do
(74) *Attorney, Agent, or Firm* — Seyfarth Shaw LLP

(57) ABSTRACT

The present invention relates to a method for purifying biomolecules or for analyzing whether an aqueous phase contains biomolecules by means of magnetic separation. The invention further relates to uses, to devices, and to kits that relate to the method according to the invention.

19 Claims, 1 Drawing Sheet

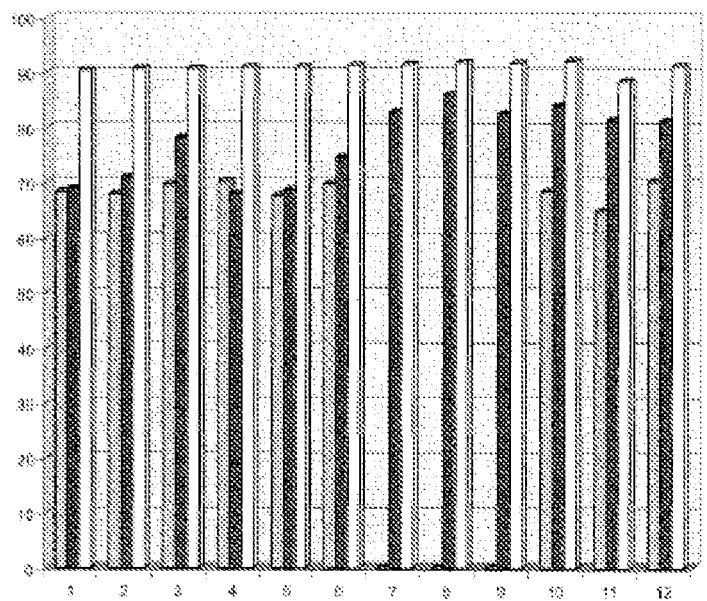

LAYERING FOR SEPARATING PARTICLES

CROSS-REFERENCE TO RELATED APPLICATION

This application is a National Stage of PCT/EP2010/053865, filed Mar. 25, 2010, which claims priority to German Patent Application No. 10 2009 001 864.6, filed Mar. 25, 2009, the disclosures of each which are incorporated herein by reference in their entireties.

The invention relates to a method for purifying biomolecules or for analyzing whether an aqueous phase contains biomolecules, wherein an aqueous phase containing magnetic particles and any possible biomolecules is subjected to removal of the particles using a magnetic rod, characterized in that the aqueous phase is overlaid with an organic phase and that the magnetic rod is guided through the organic phase during the removal of the particles from the aqueous phase. The invention also relates to uses, apparatuses and kits which relate to the method according to the invention.

The prior art discloses biochemical purification methods in which biomolecules bind to magnetic particles. Various methods are used in order to subsequently remove the magnetic particles with the biomolecules bound thereto from the aqueous solution.

Promega offers a purification system for isolating DNA from PCR samples under the brand name "Wizard MagneSil PCR Clean-Up System". Here, magnetic particles are added to a PCR sample. Using a magnet which contacts the sample vessel from the outside, the magnetic particles are fixed to one side of the vessel. The aqueous supernatant is removed, while the particles remain in the vessel. Subsequently, wash steps are carried out and the DNA is eluted from the particles in the same sample vessel.

Based on the sample principle is a purification system offered by Macherey-Nagel under the brand name "NucleoMag 96 PCR", for DNA from PCR samples. Here as well, the magnetic beads are bound to a vessel wall, while the supernatant is removed using a pipet.

A further method for isolating nucleic acids from biological samples using magnetic particles is used in a method which is offered by QIAGEN in a kit, for example a QIAsymphony Virus/Bacteria Kit or a QIAsymphony DNA or RNA Kit, etc. Here, a biological sample containing nucleic acids is admixed with magnetic particles which bind nucleic acid. The particles are subsequently removed using a magnetic rod. The magnetic rod is dipped into the sample vessel and moved up and down in order to fully bind the particles. Afterwards, the rod with the particles bound thereto and the nucleic acid bound thereto are pulled out or the sample vessel and transferred to a second sample vessel. In the second reaction vessel, the nucleic acid is eluted using suitable aqueous solutions. Subsequently, the magnetic rod is removed from the eluate.

With the known method of removing magnetic particles and biomolecules bound thereto using a magnetic rod, there is the problem that the magnetic rod undesirably carries over the aqueous solution. Thus, along with the rod, there is removed an irregular portion of the aqueous phase, which portion wets the rod and the particles bound thereto. This carryover of a portion of the aqueous solution with the beads and the magnetic rod is essentially based on physical phenomena. During the removal of the magnetic rod, aqueous solution accumulates at the magnetic rod until irregular breakup of a droplet occurs. Further inaccuracies may arise when, depending on the application, the particles are air dried for a few minutes prior to elution.

In particular, it is problematic that the amount of the transferred aqueous phase is irregular. Thus, irregular amounts of further, undesired constituents are removed from an aqueous phase at the same time. During elution of biomolecules to be isolated and subsequent analysis, the result may, as a consequence, be altered not only quantitatively but also qualitatively. In addition, downstream reactions or diagnostic results may be altered and distorted. Particularly for sensitive applications, such as the detection of viruses and pathogens for example, the inaccuracies described may result in those methods with a magnetic rod involving variations and losses in sensitivity. This affects in particular methods in which low elution volumes are selected for very-high concentration of biomolecules.

Particularly when using samples having a high concentration of impurities, for example in the case of cell lysates, there is the risk that undesired constituents, such as cell walls, nucleic acids or proteins, unspecifically attach/adhere to the magnetic beads or hind thereto and are undesirably-transferred or carried over.

The problem of carrying over part of the aqueous solution can he seen particularly when removing the magnetic rod with magnetic particles hound thereto from eluates in which a hiomolecule isolated beforehand with the magnetic particles is present. Such eluates often have a relatively low liquid volume, and so the carryover of part of the aqueous phase distinctly distorts the concentration of the isolated biomolecule in the eluate.

The object of the invention is to provide a method which overcomes the problems described. The accuracy of the known methods for removing biomolecules is to be improved. In particular, high reproducibility is to be achieved for a multiplicity of samples. Methods according to the invention for isolating biomolecules and for analyzing whether biomolecules are present in a sample should he minimally impaired by inaccuracies, of liquid volumes for example. The invention should make it possible to simplify the known methods and to carry them out more efficiently.

The object addressed by the invention is surprisingly achieved by methods and uses having the features of claims 1 to 15.

The invention provides a method for purifying biomolecules or for analyzing whether an aqueous phase contains biomolecules, wherein an aqueous phase containing magnetic particles and possibly biomolecules is subjected to removal of the particles using a magnetic rod, wherein the aqueous phase is overlaid with an organic phase and the magnetic rod is guided through the organic phase during the removal of the particles from the aqueous phase.

In one embodiment of the invention, the biomolecules are not bound to the magnetic particles during removal of the magnetic particles using the magnetic rod and remain in the aqueous phase. In this embodiment, the biomolecules, bound to the magnetic particles, were preferably removed in a preceding step from a first aqueous phase using the magnetic rod. The biomolecules were then transferred to the second aqueous phase, in which they are separated (eluted) from the magnetic particles. This (second) aqueous phase, which is or becomes overlaid with the oil phase, is therefore an eluate.

In a further embodiment of the invention, the biomolecules are bound to the magnetic particles during the removal of the magnetic particles and are removed from the aqueous phase with the magnetic particles. In this embodiment, the aqueous phase is preferably a lysate or a reaction mixture, from which a released biomolecule or a reaction product is to be removed.

The method according to the invention can be used both for isolating biomolecules and for analyzing whether a sample comprises biomolecules. For biochemical methods, more particularly diagnostic methods, it is often unknown at the beginning whether a sample contains the target biomolecule or not. According to the invention, methods in which the biomolecule to be purified (cleaned up) is not obtained are also considered to be methods "for isolating" said biomolecule, since the initial intention when carrying out the method is isolation. Methods according to the invention for analysis are, in particular, diagnostic methods, for example to determine whether a sample contains viruses, bacteria or other pathogens or constituents thereof, or markers which are indicators of diseases. According to the invention, the expression that a sample "possibly contains biomolecules" means that a sample "contains biomolecules or is suspected of containing biomolecules".

The magnetic rod is guided through the organic phase during the removal of the particles from the aqueous phase. In this step, the magnetic particles, possibly with biomolecules to be isolated bound thereto, are bound to the magnetic rod.

The organic phase displaces the aqueous phase when the magnetic rod passes and thus prevents the "carryover" of the aqueous phase.

When biomolecules are attached or bound to the magnetic particles and are removed from the solution, the organic phase prevents impurities from the aqueous phase from being isolated with the biomolecules bound to the magnetic particles. Although, instead of the aqueous phase, a small portion of the organic phase is transferred with the magnetic rod, there is interference with downstream reactions. Firstly, after transfer of the particles to another aqueous phase, the organic liquid accumulates on the surface thereof and can be easily removed; secondly, the organic liquid itself usually does not contain any interfering impurities. The method according to the invention distinctly reduces the undesired transfer of aqueous solution and impurities with the magnetic rod. The portion of the aqueous phase remaining. the starting solution is, for multiple samples, very uniform and distinctly larger than for conventional methods. Furthermore, according to the invention, eluates of higher purity are obtained with direct isolation of biomolecules from reaction mixtures and lysates. Therefore, the method according to the invention using an organic phase can, in contrast to known methods, additionally avoid wash steps.

A further advantage of the method according to the invention is that, immediately after the biomolecules to be isolated have been removed using the magnetic rod through an organic phase, there is no possibility of further reactions between said molecules and constituents of an aqueous phase that is carried along. If, as for known methods, remnants of an aqueous phase are carried over with the magnetic rod, interactions or reactions which distort the results, for example between nucleic acids to be isolated and proteins that are carried along, may, in contrast, still occur until the biomolecules are eluted.

When magnetic particles are removed from an eluate using a magnetic rod and pass an organic phase, this ensures that the eluate amount is not altered or only negligibly altered. Thus, there is also undesired removal of biomolecules.

According to the invention, "biomolecules" means molecules which may be identical or else a mixture, such as, for example, nucleic acids, more particularly a DNA or RNA fraction, proteins, sugars, or metabolites. In preferred embodiments of the invention, the biomolecules are free or bound biopolymers, more particularly nucleic acids, which are preferably natural or vitro treated, or proteins, or sugars. In the context of the present invention, biopolymers are understood to mean naturally occurring macromolecules—such as nucleic acids, proteins, or polysaccharides—and synthetically produced—such as, for example, fermentation process-generated—polymers which contain the same or similar building blocks, such as natural macromolecules. According to the invention, the biomolecules may also be constituents of complexes, such as protein complexes, viruses, or nucleic acid/protein complexes, and are isolated as such.

The nucleic acids are preferably natural, more particularly linear, branched or circular, nucleic acids, such as DNA and/or RNA. The DNA can, for example, be genomic DNA or plasmid DNA. The DNA can also be a product of enzymatic reactions, for example amplified DNA from a PCR sample or fragments from an enzyme digest. The RNA can, for example, be mRNA or noncoding RNA, such as, for example, miRNA, rRNA, siRNA, snRNA, snoRNA, piRNA, tRNA, hnRNA, or ribozymes.

In general, biomolecules can be attached or bound to the magnetic particles according to known methods, with use being made of, for example, ionic interactions, hydrogen bonds, hydrophilic or hydrophobic bonds, affinity bonds, or covalent bonds. For simplification, the term "bind" is used hereinafter and in the context of this application for any type of attachment or binding.

The aqueous phase used can be any aqueous solution which is used in biochemical or diagnostic methods and assays and which contains biomolecules. The aqueous solution can, for example, be a cell, bacteria or tissue lysate, a body fluid, an in vitro reaction mixture, or a fraction of one of said solutions. In general, the aqueous solutions can also be obtained from the aforementioned sources by purification and separation steps. Suitable aqueous solutions are also those in which known biochemical reactions, more particularly enzymatic reactions, have been carried out. In a preferred embodiment, the aqueous phase is an eluate, more particularly one which is obtained upon addition of an elution solution to magnetic particles.

Suitable organic phases are in principle liquids or mixtures of liquids which are substantially immiscible with water and, upon addition to water, form an upper phase with a distinct phase boundary. In preferred embodiments of the invention, the organic phase contains hydrocarbons, more particularly saturated hydrocarbons, or consists of them. Suitable hydrocarbons are branched or unbranched, substituted or unsubstituted, acyclic or cyclic hydrocarbons having 5, 6, 7, 8, 9, 10, 11, 12, 13, 14, 15, 16, 17, 18, 19, or 20 carbon atoms. Preference is given to branched or unbranched, substituted, acyclic or cyclic hydrocarbons having 6, 7, 8, 9, 10, 11, 12, 13, 14, 15, or 16 carbon atoms. Particular preference is given to unsubstituted, acyclic, branched or unbranched hydrocarbons having 8, 9, 10, 11, or 12 carbon atoms, of which n-octane, n-nonane, n-decane, and mineral oils are very particularly preferred. In the context of the present invention, mineral oils are understood to mean the liquid distillation products which are obtained from raw mineral materials—such as crude oil, lignite and coal, wood, or peat—and which consist essentially of mixtures of saturated hydrocarbons (cF. Römpp, Lexikon Chemie [Encyclopedia of Chemistry], Thieme Verlag, Stuttgart).

The organic phase can also contain silicone oil or consist of it:. Silicone oils are suitable, since they are, to a great extent, inert toward other substrates and have a high spreading capacity which is associated with the formation of particular properties, for example hydrophobicity. Suitable silicone oils are, in particular, synthetic oils based on semi-organic polymers and copolymers comprising silicon-oxygen units having organic side chains. Preference is given to polymers or copolymers comprising unbranched chains constructed of alternating silicon and oxygen atoms. The polymers have in particular chain lengths of from 10 to 1000, preferably from 30 to 500, particularly preferably from 50 to 150, silicon atoms.

Overlaying aqueous phases with organic phases has already been described in the prior art in the area of biochemistry. However, overlaying was carried out for different purposes and in different methods than those for the present invention. More particularly, use of an organic phase in purification methods with magnetic beads was unknown. For instance, the European patent application EP 1 559 478 A1 discloses the use of hydrocarbons as a contamination barrier. Overlaying aqueous solutions with hydrocarbons avoids impurities occurring owing to carryovers or aersol formations when processing large numbers of samples, such as in high-throughput screening.

The European patent application EP 1 256 627 A1 relates to the use of hydrocarbons for preventing cross-contaminations. Here, when using sample vessels which have an outlet at the bottom side, overlaying a sample with alkanes achieves a more uniform and more complete removal of the aqueous phase through the outlet.

In a preferred embodiment of the invention, the magnetic particles are silica particles. According to the prior art, these are used in particular for binding nucleic acids. Magnetic silica particles for binding nucleic acids are commercially available and are, for example, offered by QIAGEN in kits having the brand name "MagAttract". Such particles are also referred to as "beads". However, according to the invention, use can be made of all known magnetic particles which are capable of binding biomolecules.

According to the invention, the magnetic rod which can used is any elongated apparatus which, upon introduction into a sample vessel, is suitable for removing magnetic particles from the sample vessel. The magnetic particles can bind to the magnetic rod on a magnetic rod protector which has been fitted to the magnetic rod.

In one embodiment of the invention, the rod is guided through the aqueous phase and the organic phase. In a further embodiment, the rod is guided only through the organic phase without coming into contact with the liquid phase. In a further embodiment, the rod is guided through the organic phase and the boundary area of the phases, passing through the liquid phase in the dipping direction by not more than 2%, 3%, 4%, 5%, 6%, 10%, 15%, or 20%. It was observed that the carryover of the aqueous phase can be minimized when the the liquid phase is not completely passed through.

According to the invention, after the removal of the magnetic particles with biomolecules bound thereto from the solution, there preferably takes place further cleanup, analysis or processing according to known methods. These comprise elution of the biomolecules, wash and purification steps, analysis of the type and amount, and carrying out further reactions. According to the invention, the removal (elution) of the biomolecules from the magnetic particles is preferably followed by further cleanup, analysis or processing according to known methods. These comprise wash and purification steps, analysis of the type and amount, and carrying out further reactions.

The aqueous phase is, for example, contained in a sample vessel which has an empty volume of from 100 µl to 3000 µl. Particular preference is given to empty volumes between 500 µl and 1500 µl. This corresponds to customary sample vessels which are used on a laboratory scale for studying or processing a multiplicity of samples. The volume of the aqueous phase in the sample is preferably between 10 µl and 1000 µl, more particularly between 50 µl and 750 µl.

In preferred embodiments of the invention, the organic phase is used in an amount of from 100 µl to 500 µl. Preferably, the amount of organic phase is selected such that the aqueous phase is completely overlaid. When using customary sample vessels on a laboratory scale ("Eppendorf tubes"), more than 200 µl or more than 250 µl are suitable in particular. Preference is given in particular to the use of an amount between 200 µl and 400 µl or between 250 µl and 350 µl. The thickness of the organic phase at the thinnest point is preferably at least 1 mm, 2 mm, 3 mm, 4 mm, or 5 mm.

In one embodiment of the invention, after the addition of the magnetic particles to the aqueous phase and/or the overlaying of the aqueous phase with the organic phase and before the removal of the particles using the magnetic rod, there is no carrying out of a chemical reaction, more particularly an enzymatic reaction, such as a PCR reaction for example. This means that chemical reactions are not initiated in this period, for example by addition of reagents such as enzymes. Naturally, it cannot be excluded that reactions which commenced before this period do not proceed further to a slight extent. However, a reaction can actively carried out which triggers or supports the detachment of the biomolecules from the magnetic particles.

In one embodiment of the invention, no PCR reaction was carried out in the aqueous phase before carrying out the method and/or the biomolecule to be isolated is not a PCR product. In the known PCR reactions, samples are overlaid with mineral oil in order to prevent the evaporation of aqueous solutions at the high temperatures used. According to the prior art, after carrying out a PCR reaction, the amplicon is, however, not transferred through the mineral oil with a magnetic rod, but rather the aqueous phase is first pipetted off under the organic phase and the mineral oil is discarded.

According to the invention, the magnetic particles can first be added to the aqueous phase and the sample can then be overlaid with the organic phase. However, according to the invention, it is also possible first to overlay the aqueous phase with the organic phase and only then to add the magnetic particles, for example by pipetting directly into the aqueous phase.

In a further embodiment of the invention, the overlaying of the aqueous phase with the organic phase and/or the addition of the magnetic particles is followed by a reaction, for example an enzymatic reaction such as a PCR reaction. For example, a PCR reaction can be carried out under customary conditions, with the PCR sample being overlaid with an organic phase. After the reaction has ended, the magnetic particles are added to the PCR sample to bind the DNA. The particles with the DNA bound thereto are subsequently removed through the organic phase using the magnetic rod. In this embodiment of the invention, the organic phase serves both as an evaporation barrier for the PCR reaction and to improve the accuracy of the removal of the DNA from the solution.

In a preferred embodiment of the invention, the method is automated.

The method according to the invention for purifying biomolecules from an aqueous phase or for analyzing whether an aqueous phase contains biomolecules comprises more particularly the following steps:
(a) providing a first aqueous phase, which contains biomolecules, in a first reaction vessel,
(b) adding magnetic particles,
(c) removing the magnetic particles with biomolecules bound thereto from the aqueous phase using a magnetic rod,
(d) transferring the magnetic particles with the biomolecules bound thereto to a second reaction vessel,
(e) eluting the biomolecules from the magnetic particles in a second aqueous phase in the second reaction vessel,
(f) removing the magnetic particles from the second reaction vessel using the magnetic rod, with the biomolecules remaining in the (second) aqueous phase,
wherein prior to step (c) the first aqueous phase is overlaid with an organic phase, and the magnetic rod is guided through the organic phase during the removal of the particles from the first aqueous phase, and/or
prior to step (f) the second aqueous phase is overlaid with an organic phase, and the magnetic rod is guided through the organic phase during the removal of the particles from the second aqueous phase.

The steps of the method are passed through in the order (a) to (f). The addition of magnetic particles and the overlaying of the aqueous phase is carried out according to known methods, for example using a pipet. Afterwards, the aqueous phase can be incubated. After step (b), a magnetic rod is introduced into the first aqueous phase. The rod is preferably moved in order to achieve full binding of the magnetic particles.

Prior to step (c), in the first reaction vessel, conditions are set, under which the biomolecules bind to the magnetic particles (step (b1)). The binding is preferably achieved selectively. In steps (c) and (d), the rod with the particles and the biomolecules bound thereto is removed and transferred to a second reaction vessel in which the elution (e) of the biomolecules is carried out. For the elution (e), conditions are set which impair the interaction between the magnetic particles and the biomolecules bound thereto. In the case of nucleic acids bound to silica particles, the elution is achieved by, for example, alteration of the salt concentration. Prior to the elution of the biomolecules (e), one or more wash steps can be carried out.

According to the prior art, methods having steps (a) to (f) without overlaying an aqueous solution with an organic phase are known. Such a method is, for example, used in the kit offered by QIAGEN under the name "QIAsymphony DNA Kit". Reference is explicitly made here to the method described in the accompanying handbook (May 2008). In at least one downstream step (g), for example, the analysis to determine whether the biomolecules are present in the eluate can follow. Further purification steps or downstream reactions can also follow.

The invention also provides the use of an organic liquid immiscible with water for improving the accuracy of a method in which biomolecules which are bound to magnetic particles are removed from an aqueous phase using a magnetic rod. The method according to the invention ensures in particular that uniform and only very low amounts of aqueous solution are removed from the starting solution using the magnetic rod. The improvement in accuracy therefore lies in a particularly uniform volume of the overlaid aqueous solution, more particularly of an eluate, and in the minimization of the proportion of impurities.

The invention also provides an apparatus for purifying biomolecules from an aqueous phase or for analyzing whether an aqueous phase contains biomolecules, comprising at least one reaction vessel containing an aqueous solution, biomolecules, and magnetic particles, wherein the aqueous solution is overlaid with an organic phase which is immiscible with water, wherein the apparatus has a magnetic rod. The apparatus is, for example, a laboratory robot or an automated device which can analyze a multiplicity of samples.

The invention further provides a kit for purifying biomolecules, using a magnetic rod, from an aqueous phase or for analyzing whether an aqueous phase contains biomolecules, comprising an aqueous solution, biomolecules, magnetic particles, and an organic liquid which is immiscible with water. The kit preferably contains a magnetic rod.

FIG. 1 shows the results of exemplary embodiments 1 to 12. For each example, the left-hand bar (light gray) shows the elution volume in µl without oil overlay, the middle bar (dark gray) shows the elution volume in µl with oil overlay, and the right-hand bar (white) shows the starting volume used in µl (input volume). The measured results are, in each case, mean values from 8 samples from a process vessel (process tube).

Examples 1-3: 10 µl, 50 µl, or 200 µl of oil with separation over the oil layer.

Examples 4-6: 10 µl, 50 µl, or 200 µl or oil with separation the region of the aqueous phase.

Examples 7-9: Triplicate determination with, in each case, 300 µl of oil overlay and separation only over the oil layer.

Examples 10-12: Triplicate determination with, in each case, 300 µl of oil overlay and separation over the entire liquid.

EXEMPLARY EMBODIMENTS

Implementation

The effect of an oil overlay in the separation of magnetic particles from a nucleic acid-containing solution was determined semiautomatically on an automated sample preparation module (QIAsymphony™ SP, QIAGEN). For this purpose, a shortened procedure was programmed on the system as follows:

Firstly, the 8-well process vessels (Sample Prep Cartridges, QIAGEN) used on the instrument were each filled with 300 µl of buffer using the pipetting unit. Subsequently, the magnetic beads were mixed in the corresponding reservoir to obtain a homogeneous suspension and, in each case, 40 µl of the suspension were added to the AVE buffer (a commercially available wash and/or elution buffer, QIAGEN) which had already been initially charged. The resulting suspension was mixed for 10 sec on the instrument using the mixing unit and then, using the magnetic rods present in the mixing unit and the fitted and previously weighed magnetic rod protector (8-Rod Cover, QIAGEN), the magnetic particles were collected on the magnetic rod protector as a result of repeated passage through the liquid column and lifted out of the liquid. The magnetic particles collected on the magnetic rod protector were air dried for 8 minutes. In parallel, a further process vessel which had previously been weighed empty was prepared with the actual elution buffer AVE (91 µl) and weighed to determine the mean initial charge volume. After drying, the magnetic particles were transferred from the magnetic rod protector to the initially charged elution buffer. A further 3-minute mixing step was carried out using the mixing unit of the instrument. After the elution thus carried out, the magnetic particles were recollected on the magnetic rod protector (separation) and the eluate remaining in the process vessel was determined by weighing. Subsequently, the magnetic particles previously collected on the magnetic rod protector were again completely transferred to the eluate. Afterwards, the suspension was, in each case, manually overlaid with the same amount of mineral oil, weighed, and reseparated. After the separation, the process vessel was weighed to determine the elution amount now retained. The magnetic rod protector with the magnetic particles located thereon was released in a fresh, previously weighed process vessel and likewise weighed. So that the eluate amount retained in the sample vessel with oil overlay can be accurately determined, the process vessels were stored at about 35° C. in a drying cabinet. After complete evaporation of the aqueous phase, the weight was determined until constant.

Firstly, the effect of the oil amount on the recovered eluate should be checked. For this purpose, 10 µl, 50 µl, and 100 µl of mineral oil were pipetted onto the respective eluates of a process vessel. The three process vessels, each with 8 eluates, were conducted simultaneously through the above-described process. Here, the beads were separated by the liquid column of the aqueous phase (91 µl) being completely passed through, starting from the vessel base. In a further experiment, using the same experimental arrangement, about half the liquid column of the aqueous phase (50 µl) was passed through during the separation, starting from the vessel base.

In a third experiment, the effect of the type of separation was to be studied further. For this purpose, a modification was made of the software-anchored separation procedure. The separation was not to be achieved as usual over the liquid column seen from the base, but only over the oil phase. In this experiment, an oil volume of 300 µl was used for the complete overlaying of the elution volume used and the separation was carried out over the liquid column of the oil with an offset from the base of 96 µl (aqueous phase) up to a maximal fill height of 421 µl. In addition, the magnetic rod protector with the inserted magnetic rods waited for 3 sec at the upper point of the separation (421 µl) in order to pull as much magnetic particles as possible from the aqueous phase through the entire liquid column of the oil.

Owing to the difficulty of an intervention in the regular separation procedures, in a further experiment with an oil volume of 300 µl, the complete liquid column from the vessel base up to an upper point of the liquid column of 421 µl was passed through.

Results

Examples 1 to 6

In a first series of experiments, the effect of the oil amount on the displacement of the aqueous phase from the magnetic particles was analyzed (FIG. 1, examples 1-3). Separation was achieved over the entire liquid column consisting of aqueous phase and oil phase. It could be clearly seen that the oil in low amounts of 10 µl or 50 µl has only a marginal effect on the retained eluate amount (aqueous phase) (middle dark gray columns). The retained eluate amount without an oil layer (left-hand light gray columns) corresponded to the elution amounts which were to be expected for elution disclosed by the prior art, without an oil layer. Larger oil amounts achieved, by contrast, a significant increase in the retained volume (see in particular FIG. 1, example 3/middle dark gray column).

In a second series of experiments, different oil volumes were likewise selected. In addition, separation was carried out only in the region of the aqueous phase (FIG. 1, examples 4-6). Here, the tendency was to the same result, but the effects were less strongly pronounced.

The two series of experiments clearly showed that oil volume is of particular importance. Observations of the course of events during separation suggested that a closed oil cover over the aqueous phase has a very positive effect on the displacement of the aqueous phase from the magnetic particles. In the case of a low oil amount, the aqueous phase, owing to the surface tension with the magnetic particles upon withdrawal of the magnetic rod protector, is pulled along upward, and the oil loses its positive effect on the displacement of the aqueous phase from the magnetic particles.

Examples 7 to 9

In a third series of experiments, the oil volume was markedly increased so that a closed oil phase over the aqueous phase was obtained and so that the effect on the subsequent separation of the magnetic particles through the oil layer could be used. In order to particularly intensify this effect, separation should be achieved substantially over the oil layer. For this purpose, the procedure on the instrument for separation was altered such that the magnetic rod protector with inserted magnetic rods moves only through the oil phase and received only slight direct contact with the aqueous phase. Furthermore, the magnetic rod protector with inserted magnetic rods was also left for 3 s at the oil surface prior to the actual movement of separation in order to achieve a first accumulation of the magnetic particles at the boundary between of phase and aqueous phase. Since the measurement was made only over the oil phase, a direct reference measurement without the oil phase was not possible this experiment. The result in (FIG. 1, examples 7-9) shows a significant rise in the retained eluate amount (about 91% of the elution volume used). Only a small portion is lost as a result of the adhesion to the magnetic particles. Compared to conventional elution without an oil overlay, an increase of about 15% for the recovered eluate was recorded.

Examples 10 to 12

Owing to the difficulty that specific separation conditions were required in examples 7 to 9, the further examples 10 to 12 made use of an increased oil amount (300 µl) in a conventional separation. As in examples 7 to 9 a pause of 3 s at the oil surface for the magnetic rod protector was provided prior to the actual movement of separation. The results show a negligible reduction of the retained eluate amount (FIG. 1: examples 10-12). About 90% of the eluate was retained.

The experiments show that the overlaying of a magnetic particle-enriched aqueous phase with mineral oil helps, during the removal of the magnetic particles using a magnetic rod, to substantially displace the aqueous phase from the magnetic particles. Here, two effects in particular are important. Firstly, it is prevented by the oil layer that parts of the aqueous phase, owing to the asymmetric accumulation of the magnetic particle (bead pellet), are not carried over in an upward direction via capillary forces in the aqueous phase between the protruding bead pellet and the vessel wall and cause, in unfavorable cases, droplet breakup, so that the aqueous solution remains on the bead pellet and is therefore lost. Secondly, oil layer achieves a displacement of the aqueous phase from the magnetic particles. This positive effect is particularly pronounced when the oil amount is sufficient for a closed overlaying of the aqueous phase. Even better results are achieved when, during the separation of the magnetic particles through the oil layer, the magnetic rod does not pass through the aqueous phase for better collection of the remaining particles.

The invention claimed is:

1. A method for purifying target biomolecules from an aqueous phase, or for analyzing whether an aqueous phase contains target biomolecules, the method comprising:
   (a) providing a vessel comprising an aqueous phase containing magnetic particles and possibly target biomolecules, wherein the aqueous phase is overlaid with an organic phase and wherein target biomolecules present in the aqueous phase bind to the magnetic particles;
   (b) guiding a magnetic rod through the organic phase;
   (c) binding the magnetic particles to the magnetic rod, wherein the magnetic articles are not fixed to a side of the vessel by a magnet prior to the binding;
   (d) removing the bound magnetic particles from the aqueous phase by passing the magnetic rod and the bound magnetic particles through the organic phase, thereby displacing any aqueous phase from the magnetic particles so as to prevent carry-over of the aqueous phase; and
   (e) when the method is for analyzing, further comprising analyzing whether the target biomolecules are present.

2. The method as claimed in claim 1, wherein the target biomolecules are or comprise nucleic acids, proteins, or sugars.

3. The method as claimed in claim 1, wherein the aqueous phase comprises a cell lysate, a bacteria lysate or a tissue lysate, a body fluid, or an in vitro reaction mixture.

4. The method as claimed in claim 1, wherein the organic phase contains hydrocarbons and/or silicone oil.

5. The method as claimed in claim 1, wherein the magnetic particles are silica particles.

6. The method as claimed in claim 1, wherein the aqueous phase is completely overlaid with the organic phase.

7. The method as claimed in claim 1, wherein after the providing of the vessel in (a) and before the removal of the bound magnetic particles in (d), there is no carrying out of a chemical reaction or an enzymatic reaction in the aqueous phase.

8. The method as claimed in claim 1, wherein the method is automated.

9. The method as claimed in claim 1, wherein the biomolecule to be isolated is not a PCR product.

10. The method as claimed in claim 9, wherein no PCR reaction is carried out in the aqueous phase after adding the magnetic particles to the aqueous phase.

11. A method for purifying target biomolecules from an aqueous phase, or for analyzing whether an aqueous phase contains target biomolecules, the method comprising:
   (a) providing a first vessel comprising a first aqueous phase, which possibly contains target biomolecules,
   (b) adding magnetic particles to the first aqueous phase, wherein target biomolecules present in the first aqueous phase bind to the magnetic particles,
   (c) binding the magnetic particles to a magnetic rod, wherein the magnetic particles are not fixed to a side of the vessel by a magnet prior to the binding,
   (d) removing the bound magnetic particles with target biomolecules bound thereto from the first aqueous phase,
   (e) transferring the magnetic particles with the target biomolecules bound thereto to a second reaction vessel comprising a second aqueous phase,
   (f) eluting the target biomolecules from the magnetic particles into the second aqueous phase,
   (g) binding the magnetic particles to a magnetic rod, wherein the magnetic particles are not fixed to a side of the vessel by a magnet prior to the binding,
   (h) removing the bound magnetic particles from the second reaction vessel using the magnetic rod, with the target biomolecules remaining in the second aqueous phase, and
   (i) when the method is for analyzing, further comprising analyzing whether the target biomolecules are present,
   wherein prior to the binding in (c) the first aqueous phase is overlaid with an organic phase, and the magnetic rod is guided through the organic phase prior to the removal of the bound magnetic particles from the first aqueous phase, and/or prior to the binding in (g) the second aqueous phase is overlaid with an organic phase, and the magnetic rod is guided through the organic phase prior to the removal of the bound particles from the second aqueous phase, and wherein the removing the bound magnetic particles in (d) and/or in (h) comprises passing the magnetic rod and the bound magnetic particles through the organic phase thereby displacing any aqueous phase from the magnetic particles so as to prevent carry-over of the aqueous phase, wherein the organic phase contains hydrocarbons and/or silicone oil.

12. The method as claimed in claim 11, wherein the target biomolecules are or comprise nucleic acids, proteins, or sugars.

13. The method as claimed in claim 11, wherein the aqueous phase comprises a cell lysate, a bacterial lysate, or a tissue lysate, a body fluid, or an in vitro reaction. mixture.

14. The method as claimed in claim 11, wherein the magnetic particles are silica particles.

15. The method as claimed in claim 11, wherein the aqueous phase is completely overlaid with the organic phase.

16. The method as claimed in claim 11, wherein, after the providing of the first vessel in (a) and before the removal of the bound magnetic particles in (d), there is no carrying out of a chemical reaction or an enzymatic reaction in the first aqueous phase.

17. The method as claimed in claim 11, wherein the method is automated.

18. The method as claimed in claim 11, wherein the biomolecule to be isolated is not a PCR product.

19. The method as claimed in claim 18, wherein no PCR reaction is carried out in the aqueous phase after adding the magnetic particles to the first or second aqueous phase.

* * * * *